United States Patent [19]

Sullivan et al.

[11] Patent Number: 6,015,916
[45] Date of Patent: Jan. 18, 2000

[54] CONSTRAINED GEOMETRY METALLOCENE CATALYST COMPLEXES

[75] Inventors: Jeffrey M. Sullivan, Loveland; Daniel Anthony Gately, Keenesburg, both of Colo.

[73] Assignee: Boulder Scientific Company, Mead, Colo.

[21] Appl. No.: 09/241,446

[22] Filed: Feb. 2, 1999

[51] Int. Cl.[7] .............................. C07F 17/00; C07F 7/28
[52] U.S. Cl. .................... 556/7; 556/11; 556/20; 556/28; 556/52; 526/126; 526/127; 526/133; 526/134; 526/160; 526/170; 526/943; 502/103; 502/117
[58] Field of Search ..................... 556/11, 7, 52, 556/20, 28; 526/126, 127, 170, 943, 160, 133, 134; 502/103, 117

[56] References Cited

U.S. PATENT DOCUMENTS

| | | | |
|---|---|---|---|
| 5,470,993 | 11/1995 | Devore et al. | 556/11 |
| 5,491,246 | 2/1996 | Rosen et al. | 556/7 |
| 5,504,224 | 4/1996 | Wilson | 556/10 |
| 5,512,693 | 4/1996 | Rosen et al. | 556/7 |
| 5,539,068 | 7/1996 | Devore et al. | 526/126 |
| 5,688,880 | 11/1997 | Spencer et al. | 526/127 |
| 5,866,704 | 2/1999 | Nickias et al. | 556/11 |

*Primary Examiner*—Porfirio Nazario-Gonzalez
*Attorney, Agent, or Firm*—Edward S. Irons

[57] ABSTRACT

A practical and scalable process for the synthesis of constrained geometry metallocene catalyst is described.

18 Claims, No Drawings

CONSTRAINED GEOMETRY METALLOCENE CATALYST COMPLEXES

RELATED APPLICATION

This application is related to commonly assigned Sullivan application Ser. No. 09/198,514 entitled "Synthesis of Tetraalkylcyclopentadienes" filed Nov. 24, 1998 (the TMCp application).

FIELD OF THE INVENTION

This invention relates to the synthesis of constrained geometry olefin polymerization catalysts which may be derived from tetraalkylcyclopentadienes. More particularly, this invention relates to the synthesis of such catalysts from tetramethylcyclopentadienes (TMCp).

BACKGROUND OF THE INVENTION

Constrained geometry olefin polymerization catalysts derived from TMCp are known. See, generally, DeVore, et al. (1995) *Organometallics* 14: 3132–3124; U.S. Pat. No. 5,470,993; European patent application 0 416 815 A2; published application Ser. No. WO98/27103; Shapiro, P. J., et al., (1990) *Organometallics* 9: 867–869; and Shapiro, P. J., et al., (1994) *J. Am. Chem. Soc.* 116: 4623–4640. The synthesis of these catalysts may include the conversion of substituted cyclopentadienyl silyl amines (CpSA ligands) of Formula I:

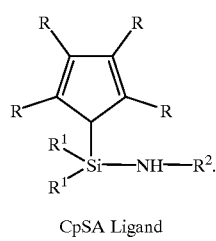

CpSA Ligand

I in which R may be an atom alkyl group, preferably having one to five carbon atoms, $R^1$ and $R^2$ are alkyl groups, wherein $R^1$ is preferably methyl and $R^2$ is preferably tertiary butyl. Each of $R^1$ and $R^2$ may be the same as or different from each other and from any R. The ligands may be converted to Group IV metal dichloride compounds of Formula II:

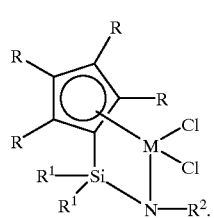

II in which M is a Group IV metal, preferably zirconium, hafnium or titanium, and R, $R^1$ and $R^2$ are as defined.

As the cited references show, the Formula II dichloride may be reacted with a diene, typically 1,3-pentadiene, to produce a constrained geometry metallocene complex useful as an olefin polymerization catalyst.

SUMMARY OF THE INVENTION

This invention provides an improved practical and scalable process for the synthesis of constrained geometry metallocene catalysts. Pursuant to the invention, an alkylcyclopentadiene, typically TMCp, may be reacted in one pot, first with n-butyl lithium and then with dimethylsilyl dichloride and an alkyl amine, preferably tert-butylamine, to produce a crude CpSA ligand of Formula I. The CpSA ligand is treated with butyl lithium and a Group IV metal tetrachloride to produce a dichloride of Formula II. The isolated Formula II compound is reacted with a diene and a butyl lithium to produce a Formula III constrained metallocene compound:

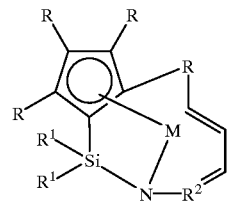

III in which M, R, $R^1$ and $R^2$ are as defined.

DETAILED DESCRIPTION OF THE INVENTION

Pursuant to one embodiment of the invention, a constrained geometry catalyst may be produced from tetramethylcyclopentadiene (TMCp) in three steps. The invention is specifically illustrated by reference to TMCp.

(1) Preparation of CpSA Ligand

TMCp is charged to a vessel, and THF is added. n-butyllithium is fed in at low temperature, preferably at a temperature of from −20° C. to −10° C. After agitation and warming to room temperature, the vessel is re-chilled to a temperature below about −10° C., and dimethyldichlorosilane is fed in at low temperature of from about −10° C. to 0° C. After agitation and warming to room temperature, the vessel is re-chilled, and t-butylamine is fed in at low −10° C. temperature. After agitation and warming to room temperature, the vessel is heated to distill THF/hexane/t-butylamine from the vessel under rough pump vacuum. Heptane is added back, and the slurry is filtered through a Buchner filter. Solids retained on the filter are washed with heptane. The vessel pressure is reduced, and a few "front ends" are collected up to a pot temperature of 100–115° C. Distilled CpSA ligand is taken off at a pot temperature of 115–125° C. with a head temperature of 95–105° C. (pot and head temperature are dependent upon actual pressure). This procedure entails Reactions 1 and 2:

Reaction 1:

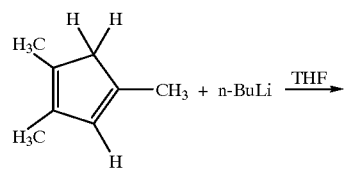

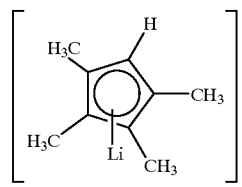 + C₄H₁₀

In this Reaction 1, any alkali metal alkyl may be used instead of n-methyl lithium. Alkali metal alkyls of one to five carbon atoms are preferred. In addition, any alkyl amine, preferably a tertiary amyl having three to six carbon atoms, may be used instead of t-butyl amine.

Reaction 2:

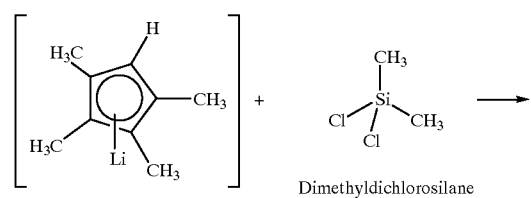

Lithium Tetramethylcyclopentadienide FW = 126.14

Dimethyldichlorosilane FW = 129.06

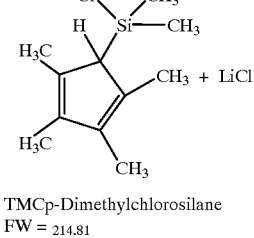 + LiCl

TMCp-Dimethylchlorosilane FW = 214.81

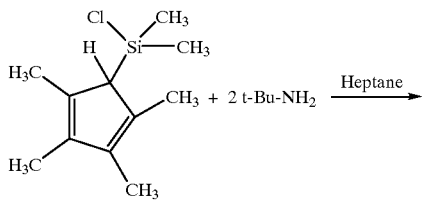

TMCp-Dimethylchlorosilane FW = 214.81

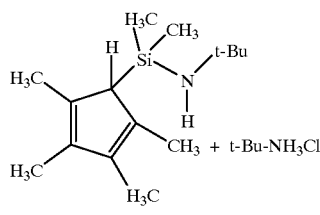 + t-Bu-NH₃Cl

CpSA Ligand FW = 252.5

(2) Preparation of the Dichloride

A second step may entail conversion of the CpSA ligand product of step I to a Formula II dichloride by treatment of the ligand with a butyl lithium and a DME complex of a Group IV metal tetrachloride, preferably titanium or zirconium tetrachloride, in a hydrocarbon solvent as illustrated by Reactions 3–5:

Reaction 3:

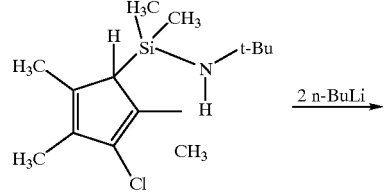

CpSA Ligand FW = 251.5

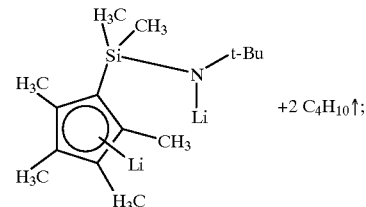 +2 C₄H₁₀↑;

Reaction 4:

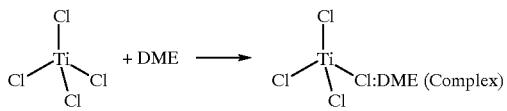

Reaction 5:

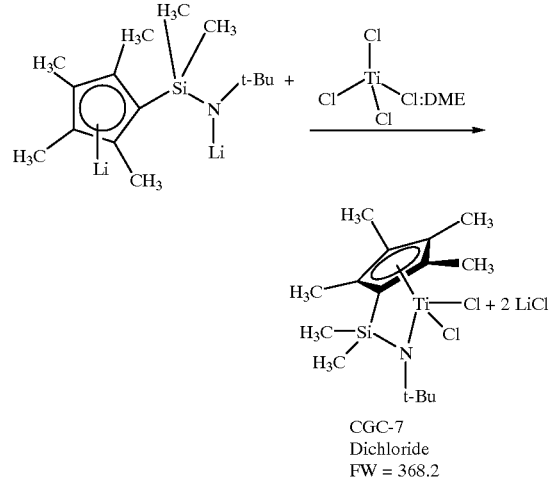

CGC-7 Dichloride FW = 368.2

Reactions 3 and 5 are preferably conducted at a temperature of from −20° C. to +10° C. Preferred hydrocarbon solvents include hexanes, heptanes and Isopar. Reaction 3 can be conducted in a mixture of Isopar E and diethyl ether, preferably in diethyl ether alone. Reaction 5 is preferably conducted in a mixture of hydrocarbon and diethyl ether.

The DME Group IV metal complex is separately prepared as a slurry in a hydrocarbon medium preferably as hexane at a temperature of 0° to −10° C. in known manner. 1.1 equivalents of DME are added to hydrocarbon solvent, followed by 1.0 equivalent of TiCl₄. The slurry is stirred for one hour at room temperature before the dilithio salt is added to this slurry.

(3) Preparation of the Constrained Geometry Catalyst

In a third step, the dichloride product of step 2 (i.e., CpSA dichloride) is converted to a Formula III constrained geometry catalyst, for example, by reaction with butyl lithium, a diene and trimethyl silicon chloride in a hydrocarbon solvent as illustrated by Reaction 6.

Reaction 6:

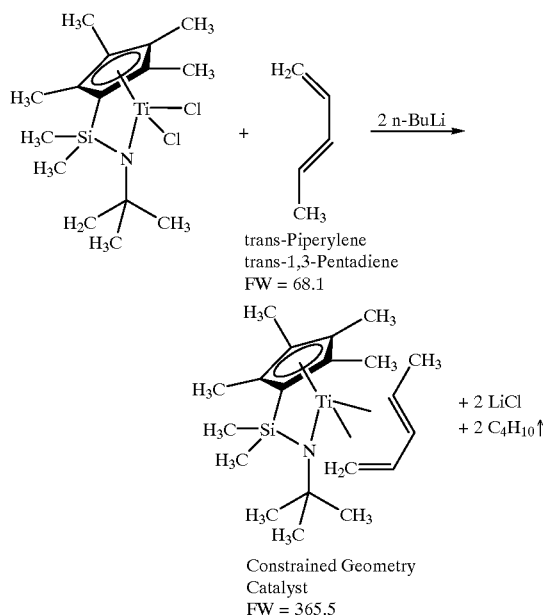

The Reaction 6 may be conducted at a temperature of −10° C. to 0° C. in hydrocarbon solvents as described for Reaction 5.

EXAMPLE 1

This example illustrates a laboratory method for conducting the Reactions 3 to 5:

Raw Materials:

| Item | Grams | Moles | Density |
|---|---|---|---|
| CpSA ligand | 25.1 | 0.1 | |
| Diethyl Ether | 14.8 | 0.2 | 0.708 |
| Isopar E | 275 (400 ml) | | 0.72 |
| n-Butyllithium | 175.5 (258.3 ml) of 1.6M in hexane | 0.413 | 0.68 |
| Titanium Tetrachloride | 18.9 | 0.1 | 1.73 |
| Dimethoxyethane | 9.45 | 0.105 | 0.86 |
| 1,3-Pentadiene, cis-/trans- mix | 7 grams contained trans-isomer | 0.108 | 0.683–0.691 |
| Chlorotrimethylsilane | 2.2 | 0.02 | 0.856 |

Procedure:

Reaction 3 (Steps 1 to 6):

1. Charge to a first clean, dry, nitrogen blanketed one liter round bottomed flask:
   25.1 grams (0.10 moles) of CpSA ligand
   275 grams (400 ml) of Isopar E,
   and 14.8 grams (0.2 moles) of diethyl ether.
2. Cool with dry ice/acetone to −10° C.
3. Feed to the flask maintaining the pot temperature below 0° C., 86.3 grams (127 ml), 0.203 moles) of n-butyllithium, 1.6 M of hexanes.
4. After the feed is complete, slowly warm the flask to 25° C. over a period of 2 hours.
5. Agitate the flask at 25° C. for 12 hours.
6. Check for reaction completion.

Reaction 4 (Steps 7 to 11):

7. Charge to a clean, dry, nitrogen blanketed 2 liter round bottomed flask:
   136 grams (200 ml) of Isopar E,
   and 18.9 grams (0.1 moles) of titanium tetrachloride.
8. Cool the second 2 liter round bottomed flask with dry ice/acetone to 0° C.
9. Feed in to the second 2 liter round bottomed flask maintaining the pot temperature at 0° C., 9.45 grams (0.105 moles) of dimethoxyethane (DME).
10. After the feed is complete, slowly warm the second 2 liter round bottomed flask to 25° C. over a period of 1 hour.
11. Agitate the 2 liter round bottomed flask at 25° C. for 2 hours.

Reaction 5 (Steps 12 to 14):

12. With both the first and second flasks at 25° C., quickly add the contents of the first 1 liter round bottomed flask to the second 2 liter round bottomed flask.
13. After step 12, agitate the second 2 liter round bottomed flask at 20–25° C. for 12 hours.
14. Heat the second 2 liter round bottomed flask distilling solvents to a pot temperature of 110° C. Hold at 110° C. for 30 minutes.

EXAMPLE 2

Preparation of the Constrained Geometry Catalyst

Reaction 6 (Steps 15 to 25):

15. Cool the step 14 2 liter round bottomed flask with dry ice/acetone to −10° C.
16. Charge to the 2 liter round bottom flask: 20 grams (7 grams contained in trans-isomer, 0.103 moles) of 1,3-pentadiene.
17. Feed 131.3 ml (0.21 moles, 89.235 grams) of n-butyllithium, 1.6 M in hexanes into the 2 liter round bottomed flask with pot temperature at maintained −10° C.
18. After the feed is complete, slowly warm the 2 liter round bottomed flask to 25° C. over a period of 1 hour.
19. Agitate the 2 liter round bottomed flask at 25° C. for 4 hours.
20. Add to the 2 liter round bottomed flask: 2.2 grams (0.02 moles) of chlorotrimethylsilane to quench unreacted or excess n-butyl (from step 17).
21. Heat the 2 liter round bottomed flask distilling solvents to a pot temperature of 110° C. Hold at 110° C. for 30 minutes.
22. Cool the 2 liter round bottomed flask to 25° C.
23. Filter through a bed of celite to a clean flask.
24. Analyze the filtrate for purity, ether content, lithium chloride content.
25. Add sufficient Isopar E to adjust the concentration of the constrained geometry metallocene product to 10% by weight. Yield: 32.9–33.6 grams, 90–92%, 0.9–0.92 moles. Theoretical yield: 36.55 grams.

EXAMPLE 3

Pilot Plant Conversion of TMCp to Constrained Geometry Metallocene

This example is a typical pilot plant conversion. Conditions may vary from batch to batch in the pilot plant.

Load 5 kg TMCp (40.91 moles) into 20 kg THF (6 gal, 20 wt% solution) in a first reactor. Cool to −20° C. under N$_2$ atmosphere.

At −20° to −10° C., add 17.0 kg (40.31 moles, 6.6 gal) of 1.6 M BuLi (calculated for 15.16% BuLi in hexane). Warm to room temperature overnight; check for completion by D$_2$O quench of a sample.

Upon completion of the BuLi addition, add 5.2 kg of dimethyldichlorosilane (40.31 moles) at −10° C. to the first reactor. Stir out overnight (at least 8 hours) with slow warm up with nitrogen bubbler, and check for completion of the reaction.

Upon completion of the reaction, add 8.84 kg of t-butyl amine at −10° C. (120.9 moles). Stir out at room temperature for at least 12 hours.

Add 20 kg heptane. Expected product is a 20 wt% CpSA solution in heptane, which is 40.5 kg heptane, and 10.13 kg CpSA. Strip THF and excess t-butyl amine via rough pump strip to a pot temperature of 40° C., using a chiller on the receiver, and water bath on the pot. Add back 30.5 kg heptane, and remove 10 kg additional heptane under rough pump. Check for a distillate "now" shot for less than 5% THF (pot should have less than 1% THF). Add more heptane as required to remove THF.

Filter over a Buchner using celite into drums. Add a 3 gallon wash of heptane (10 kg) to rinse pot and Buchner. Analyze final concentration of drums. CpSA in drums is preferably distilled under reduced pressure to yield a distilled product of higher purity.

To a second dry reactor charge 18.1 kg of diethyl ether (6.8 gallons, 15 wt%) and the distilled CpSA, 3.2 kg (11.95 moles, 0.9 gallons assuming CpSA is 94% pure).

Chill to −20° C. Add 10.3 kg of 1.6 M BuLi (4 gallons, 24.2 moles), keeping the temperature below −20° C. After feed completion, warm slowly over 2 hours to room temperature, and stir out for 12 hours under bubbler.

Into the second reactor, charge Isopar E, 16.3 kg (6.3 gallons) and TiCl$_4$ 2.2 kg (11.6 moles=should be stoichiometric). Cool to 0 to −10° C., and add dimethoxy ethane (DME, 1.1 kg, 12.2 moles). Slowly warm over 1 hour to 25° C., and stir at 20–25° C. for 2 hours.

With both reactors at −10° C., add quickly over 30 minutes the dilithio salt in the first reactor in to the TiCl$_4$-DME slurry in the second reactor keeping temperature below 0° C. Stir for 12 hours at tower water temperatures. Distill atmospherically to a pot temperature of 120° C., and hold at 120° C. for 30 minutes. It is preferred to remove all diethyl ether (leaving Isopar as solvent) before proceeding. The dichloride can be isolated as a solid by cooling the Isopar solution to −20° C. and collecting the solid by filtration under nitrogen.

If the dichloride is isolated, dissolve the solid in 16.3 kg (6.3 gallons) of Isopar E. Chill the Isopar E solution of the CGC-7 dichloride to −10° C. Charge 1,3-pentadiene 2.4 kg (837 g contained, 12.3 moles) to the contents of the second reactor. Add 1.6 m BuLi 10.7 kg (25.1 moles), keeping at −10° C. Warm to 25° C., and stir out 4 hours at 25° C. Add TMSCl 263 g. Heat to strip 120° C. pot. Hold at 120° C. for 90 minutes. Cool to 25° C. Filter through a bed of oven dried celite. Adjust concentration of catalyst product to 10% in Isopar E.

We claim:

1. A method for synthesizing a Group IV metal complex containing a tetraalkylcyclopentadiene dimethylsilyl amine ligand which comprises:

(i) reacting a tetraalkylcyclopentadiene with an alkali metal alkyl and dimethylsilyl chloride and an alkyl amine in the presence of a non-interfering medium
      wherein a first reaction mixture is produced which contains a tetraalkylcyclopentadiene silyl amine of Formula I:

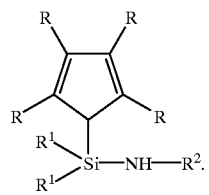

wherein R and R$^2$ are the same or different alkyl groups and R$^1$ is methyl;

(ii) reacting said tetraalkylcyclopentadiene silyl amine produced in step (i) with an alkali metal alkyl and a MCl$_4$.DME complex
      wherein M is a Group IV metal and DME is dimethoxyethane;
      wherein said MCl$_4$.DME complex is slurried in a non-interfering medium; and
      wherein a second reaction mixture is produced which contains a compound of Formula II:

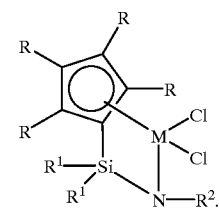

wherein R, R$^1$, R$^2$ and M are as defined; and (iii) converting said Formula II compound to a compound of Formula III:

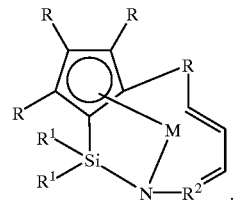

2. The method of claim 1 wherein said step (i) tetraalkylcyclopentadiene is tetramethylcyclopentadiene.

3. The method of claim 1 or claim 2 wherein the step (i) or step (ii) alkali metal alkyl is n-butyllithium.

4. The method of claim 1 or claim 2 wherein R and R$^1$ are methyl and R$^2$ is tertiary butyl.

5. The method of claim 1 or claim 2 wherein said step (i) alkyl amine is t-butyl amine.

6. The method of claim 1 or claim 2 wherein said step (i) non-interfering medium is hydrocarbon.

7. The method of claim 1 or claim 2 in which the step (ii) non-interfering medium in which said MCl$_4$.DME complex is slurried in hydrocarbon or a mixture of diethyl ether and a hydrocarbon, preferably Isopar.

8. The method of claim 1 in which said converting step (iii) is accomplished by treating said Formula II compound with an alkali metal alkyl and a diene in the absence of diethyl ether.

9. The method of claim 8 wherein said alkali metal alkyl is n-butyllithium and said diene is 1,3-pentadiene.

10. A method which comprises:

(i) reacting an alkali salt of a compound of Formula I

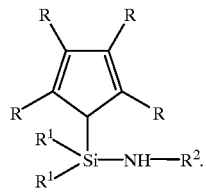

with a slurry of a $TiCl_4 \cdot DME$ adduct in a non-interfering medium wherein a reaction mixture containing a compound of Formula II

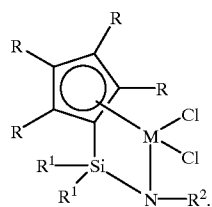

is produced.

11. The method of claim 10 wherein said alkali metal salt is a lithium salt.

12. The method of claim 10 or claim 11 wherein said non-interfering medium is a hydrocarbon medium.

13. The method of claim 10 or claim 11 wherein said non-interfering medium is Isopar E, or hexanes, or a mixture of Isopar E and diethyl ether, or a mixture of hexanes and diethyl ether.

14. The method of claim 10 or claim 11 conducted at a temperature of −20° C. to 0° C.

15. The method of claim 14, further comprising a step (ii) treating said step (i) reaction mixture with alkyl lithium and a diene, wherein a reaction mixture containing a compound of Formula III is produced.

16. The method of claim 15 wherein unreacted alkyl lithium in said reaction mixture is quenched with trimethylsilyl chloride.

17. The method of claim 1 or claim 2 wherein said step (ii) Formula II compound is not isolated from said second reaction mixture in converting step (iii).

18. The method of claim 1 or claim 2 wherein said converting step (iii) is accomplished by converting said Formula II compound in situ in said step (ii) second reaction mixture.

* * * * *

UNITED STATES PATENT AND TRADEMARK OFFICE
CERTIFICATE OF CORRECTION

| | | |
|---|---|---|
| PATENT NO. | : 6,015,916 | Page 1 of 1 |
| DATED | : January 18, 2000 | |
| INVENTOR(S) | : Jeffrey M. Sullivan et al. | |

It is certified that error appears in the above-identified patent and that said Letters Patent is hereby corrected as shown below:

<u>Column 4,</u>
Line 50, delete "CGC-7".

<u>Column 7,</u>
Line 56, delete "CGC-7" before "dichloride".

Signed and Sealed this

Fifteenth Day of October, 2002

*Attest:*

*Attesting Officer*

JAMES E. ROGAN
*Director of the United States Patent and Trademark Office*